United States Patent
Harrison, III

Patent Number: 6,004,133
Date of Patent: Dec. 21, 1999

[54] ENDODONTAL PROCEDURE WITH GRADUATED SWAB

[76] Inventor: Louie V. Harrison, III, 14 Rolling Geen Cir., Winona, Miss. 38967

[21] Appl. No.: 09/189,215

[22] Filed: Nov. 10, 1998

Related U.S. Application Data

[63] Continuation-in-part of application No. 08/736,340, Oct. 23, 1996, Pat. No. 5,833,458.

[51] Int. Cl.⁶ ........................................ A61C 5/02
[52] U.S. Cl. ........................................ 433/224
[58] Field of Search ........................ 433/102, 224, 433/72, 81

[56] References Cited

U.S. PATENT DOCUMENTS

| | | | |
|---|---|---|---|
| 2,927,056 | 3/1960 | Gurney | 167/60 |
| 4,212,639 | 7/1980 | Schaffner | 433/72 |
| 4,273,531 | 6/1981 | Hasegawa | 433/27 |
| 4,340,069 | 7/1982 | Yeaple | 128/776 |
| 4,364,730 | 12/1982 | Axelsson | 433/141 |
| 4,457,710 | 7/1984 | McSpadden | 433/81 |
| 4,462,802 | 7/1984 | Sekiya | 433/72 |
| 4,501,555 | 2/1985 | Ditchburn | 433/29 |
| 4,768,952 | 9/1988 | Lowenthal | 433/72 |
| 5,000,683 | 3/1991 | Brock | 433/72 |
| 5,096,420 | 3/1992 | Lowenthal | 433/72 |
| 5,104,322 | 4/1992 | You | 433/224 |
| 5,165,895 | 11/1992 | You | 433/49 |
| 5,423,677 | 6/1995 | Brattesani | 433/72 |

*Primary Examiner*—Nicholas D. Lucchesi
*Attorney, Agent, or Firm*—Garvey, Smith, Nehrbass & Doody, LLC

[57] ABSTRACT

An endodontal procedure wherein an absorbent dental point is having a scale of graduated depth indicators, arranged in a manner such that during the insertion of the dental point into the root canal the depth to which the tip of the dental point has been inserted into a root canal may be quickly and reliably measured each and every time a subsequent dental point is inserted in the root canal in the course of a root canal procedure.

10 Claims, 3 Drawing Sheets

ENDODONTAL PROCEDURE WITH GRADUATED SWAB

CROSS REFERENCE TO RELATED APPLICATIONS

This application is a continuation in part application of application Ser. No. 08/736,340, filed Oct. 23, 1996 which is to issue as U.S. Pat. No. 5,833,458 on Nov. 10, 1998.

STATEMENT REGARDING FEDERALLY SPONSORED RESEARCH OR DEVELOPMENT

Not Applicable.

REFERENCE TO A "MICROFICHE APPENDIX"

Not Applicable

BACKGROUND OF THE INVENTION

This invention relates to endodontal surgery and particularly to procedures and instruments employed therein including absorbent pointed probes utilized as swabs in such as root canal surgery.

While becoming less common in the developed countries through better education of the public in the care of the mouth, the inclusion of antidecay additives to such as the water supply and improvements in dental cleaners and washes, decay of the teeth still remains a common problem. When decay of a tooth is quickly noted and has penetrated the enamel (the outer hard surface of the tooth) and only nominally into the dentin (the calcareous portion as opposed to the pulp and nerve structure) repair is readily made by the treatment of cleaning out the affected tissue of the tooth, replacing it with a synthetic material (such as a dental amalgam). Thus, the tooth is said to have been filled, as by the cavity (formed by the removal of the decayed, diseased dentine) being replaced by the filling material.

If the progress of the decay of the tooth (caries) is allowed to progress into the next inner layer, i.e., the pulp containing the nerve and blood vessels, the required treatment to arrest the continuing decay is likely a "root canal", known from its inclusion in the procedure. When the decay of the tooth reaches the pulp, it likely becomes inflamed and may die. Involvement of the pulp usually results in root-end abscess and the associated infection may be passed by the blood stream to other parts of the body, producing inflammation, secondary abscess or other disease. Endodontic treatment, if initiated immediately after injury or involvement of the pulp, can prevent formation of dental abscess, or if the abscess has developed, can usually eliminate the infection without extraction of the tooth. Removal of the pulp includes removal of the live tissue including the nerves and capillary vessels of the tooth. This procedure includes the cleaning of the hollow, canal-like portions of the tooth extending into the tooth's root, by which it is anchored into the jaw bone. Once the tooth, including the root canal, is completely cleaned, the hollow is filled with an air-tight sealer (commonly including medicaments to destroy microorganisms and promote healing) and the remaining cavity filled with the amalgam, or similar material.

The process of adequately cleaning the root canal is a demanding one, requiring the absolute cleaning and sterilization of the canal, otherwise, a "dead cavity" may result. The "dead cavity" is one in which there is remaining tissue to decompose and cause further disease or abscess and may allow further decay within and adjacent the affected tooth including the surrounding periodontal tissue and occasioning the loss of supporting bone and, ultimately, the tooth. The meticulous process of the "root canal" begins with the removal of the diseased, decayed dentine by drilling and aspiration of that tissue and the underlying pulp. Firstly, the tooth is accessed through the crown of the tooth, being opened by drilling through the enamel to locate the pulp chamber. Once the pulp chamber is accessed the particular diseased canal is measured to determine the length of the canal(s) being treated. It is imperative that in the course of the endodontic procedure that the apical foramen, or opening in the canal to the periodontium, not be pierced such that the periodontium be traumatized at and during the cleaning procedure.

There are two conventional methods for determining the length of the canals. The first involves randomly placing a file in the canal and taking an x-ray to determine if the file is near the apex of the canal (beginning of the apical foramen) and repeating this procedure until the successive x-ray reveals that the file is at the apex of the canal. A rubber stopper is then placed on the "handle end" of the file, snugly against the crown of the tooth. By so noting the extent of the depth of the canal, subsequent scraping and cleaning of the canal may be carried out with assurance that the apical foramen will not be invaded in the successive scraping and cleaning. The second method for locating the depth of the canal is to use an electronic apex locator. This is an instrument which attaches to the file and electronically indicates when the apex of the canal is being approached. It is usual to additionally take an x-ray to verify the reading of the electronic measurement. As previously, a rubber stopper is placed on the file at the working distance to ensure that this extent is not exceeded potentially injuring or traumatizing the periodontium.

Several files are then prepared to the proper working depth. The capillaries and nerves contained in the interstices of the canals within the root are first loosened and scraped with narrow files. Progressively larger files are then used to enlarge the canal to completely clean out the canal and ensure that there is a good stopping point at the end of the canal for the later placement of the packing material. Once the canal is completely opened and cleaned of the with this variety of small files, the canals are then cleaned and dried with absorbent dental points, the subject of the present invention.

As explained above, the adequate cleaning of the root canal requires the dentist to probe, scrape, clean and dry the full extent of the interstices of the canal. Subsequent to the cleaning, a medicament is then applied, irrigating the canal to ensure that all debris is removed and to further sterilize the inside of the canal. Sodium hypochlorite is the solution frequently used for this purpose, taking care that it too, reaches the full extent of the canal.

Disease of the tooth, once penetrating the dentine into the pulp, allows one or more of a variety of microorganisms and bacteria to quickly infiltrate the far reaches of the canal. The same type of absorbent dental point may be utilized to deliver the medicament to the extent of the canal as was used to dry it, being typically dipped into the medicament and then routed down into the canal.

The canal is dried with absorbent "paper points". These are tightly rolled papers in the shape of an endodontic file. These paper points are sequentially placed into the canal to dry the canal of the irrigating solution. As with the files used for scraping, it is necessary to prevent the paper points from violating the apex of the canal. Accordingly, it is necessary to fashion some sort of working depth measure, as with the files. A rubber stopper may not readily or routinely be placed on the paper points for setting the working depth. It has become custom to methodically grasp the paper point with cotton pliers, carefully setting the location of each sequential grasp to the previously identified working depth to ensure paper point penetration into the canal to only the desired depth. As can be appreciated, since a dozen or more paper points are customarily cued in an endodontic procedure, the placement of the pliers and subsequent cumberson manipulation of the pliers in using the point are time consuming and restrictive. Further, the requirement for placement of the pliers accurately and ensuring that there is no slippage creates significant opportunity for error.

DESCRIPTION OF THE PRIOR ART

Absorbent dental points have been used by dentists for many years. Paper points, as they are commonly called, are conventionally formed of special types of paper or synthetic materials exhibiting similar properties. The conventional paper point should exhibit a wicking action so as to imbibe exudates present in the root canal or pulp cavity. As discussed above, the paper point should also be capable of absorbing medicaments such that they may be subsequently delivered to the selected location of the root canal. As may be expected, the point must be sufficiently stiff to be insertable into the small opening of the root canal, yet sufficiently flexible to follow the tortious path of the canal to its end. An additional quality of a suitable paper point is lateral and longitudinal strength to withstand the manipulation of the tip as treatment is effected on the root canal. This lateral and longitudinal strength must persist though the paper point is saturated with exudate or medicament.

U.S. Pat. No. 2,846,927 describes the manufacture of absorbent dental points of fibrous sheets of manila hemp, being tightly wound from a triangular sheet into an elongated, round shaft of slightly decreasing diameter from the held end to the operative or tip end.

Specialized paper points have been developed for the delivery of medicaments into the root canal. U.S. Pat. No. 5,104,322 is directed to root canal sealers and cleaners having color coded heads to permit easy identification of the diameter of the tip portion of the of the paper point. The patent distinguishes between absorbent dental points utilized as sealers, to which the disclosed invention is directed, from absorbent dental points utilized as cleaners (the primary use of absorbent points of the present invention). The patented invention teaches color coding of the heads of the points, ranging from 0.15 mm in diameter and 1.4 mm in diameter. The teaching recognizes that absorbent dental points are conventionally manufactured in lengths of approximately 28 to 30 mm.

Several patents are directed to graduated periodontal instruments for judging the depths of the effects of gingivitis and the resulting cavity created by bone loss in the affected gum adjacent a tooth. Most of these devices include mechanism for assuring that, on insertion of the probe into the diseased periodontal area, touch of the probe is maintained at a constant pressure as the probe is used to explore the bone loss associated with the disease. U.S. Pat. Nos. 5,423,677; 5,096,420; 5,000,683; 4,768,952; and 4,340,069 are illustrative of these specialized instruments.

SUMMARY OF THE INVENTION

The principal objective of the present invention is to provide a method for using and absorbent dental point instrument which includes a graduated depth scale on the shaft of the instrument by which a dentist may readily identify the depth of insertion of the tip of the instrument.

It is another object of the present invention to provide an endodontic procedure including the use of an absorbent dental point instrument, the tip of which may be selectively inserted to a predetermined depth to affect a desired treatment during root canal surgery.

It is a further object of the present invention to provide a procedure by which an absorbent dental point instrument, during the use of which, the dentist may confirm treatment to the maximum depth of the root canal.

A still further object of the present invention is the inclusion of the use of an inventive graduated depth scale on an absorbent dental point which promotes rapid and reliable reading of the depth of the tip of such a dental point.

DETAILED DESCRIPTION OF PREFERRED EMBODIMENTS

Figure 1:
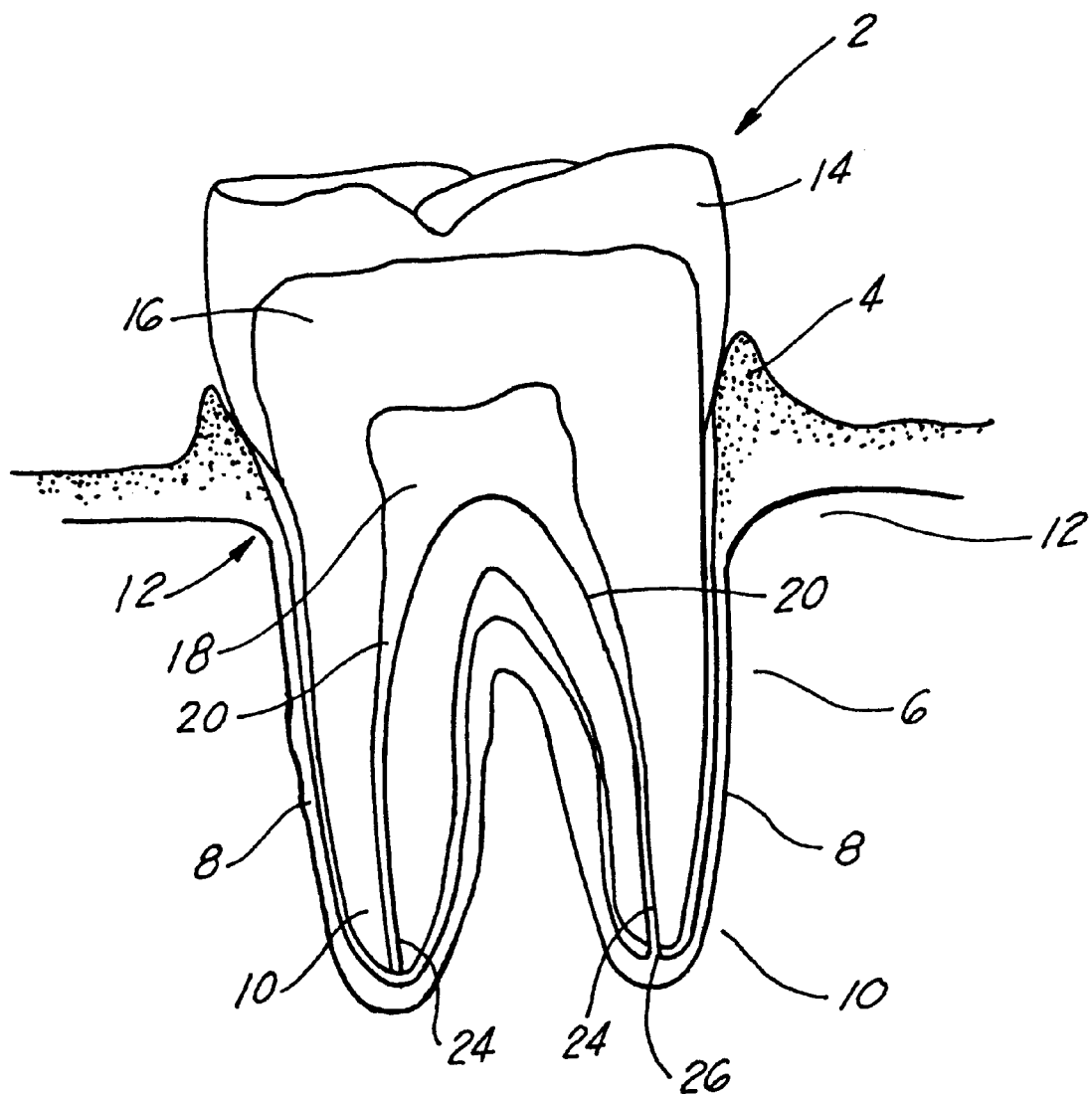
FIG. 1 is a pictorial view, partially in section, of a tooth, illustrating the tooth structure and root canal into which the present invention is inserted during use.

In order that the present invention might be better appreciated, reference is made to FIG. 1 which illustrates, in a sectional drawing, the interior of a tooth (herein a molar). Tooth 2 is anchored into gum 4 and adjacent jaw bone 6. Surrounding the tooth 2 is a periodontal membrane 8 which forms an envelope around the roots 10 of tooth 2. At the surface of the jaw bone, the periodontal membrane merges into the gum as at 12. Tooth 2 includes enamel 14, forming the hard, exterior of the tooth 2, and is composed mostly of the mineral calcium. Under enamel 14 is dentin 16 which forms the main core of tooth and it is composed generally of calcified tissue, calcium and phosphorous. The dentin 16 is highly sensitive and includes a labyrinth of tubules for the circulation of lymph.

The central structure of the tooth 2 is the nerve or, more commonly, the pulp 18. Pulp 18 is contains nerves, lymph, blood vessels and fibrous tissue. The pulp 18 is connected to the life systems through the pulp (or root) canal 20 which extends about 75% of the length of the tooth, down into the root 10 via the pulp canal 24. The pulp canal terminates in apical foramen (holes) 26 at the tip of roots 10 and through which the nerves, blood vessels and lymph join their respective systems in the body. Lining the pulp cavity is a layer of odontoblasts, whose original function was to produce the dentine and which may be activated again by such as injury or tooth decay to again begin producing a secondary, protective layer of dentin. With appreciation of the nature of the composition and extent of the pulp canal, the present invention may be better appreciated as providing an instrument which can assist the dentist in removing all of the soft tissue and contained microorganisms from the canal and dry it such that a successful sealing and immobilization of the canal may be achieved.

Figure 2:
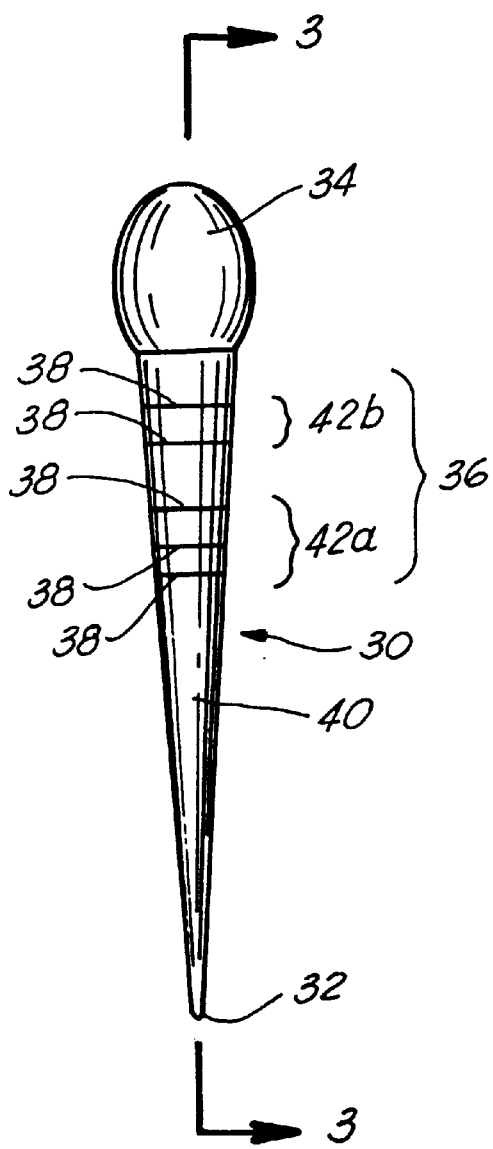
FIG. 2 is an elevational view of the absorbent dental point of the present invention.
Figure 3:
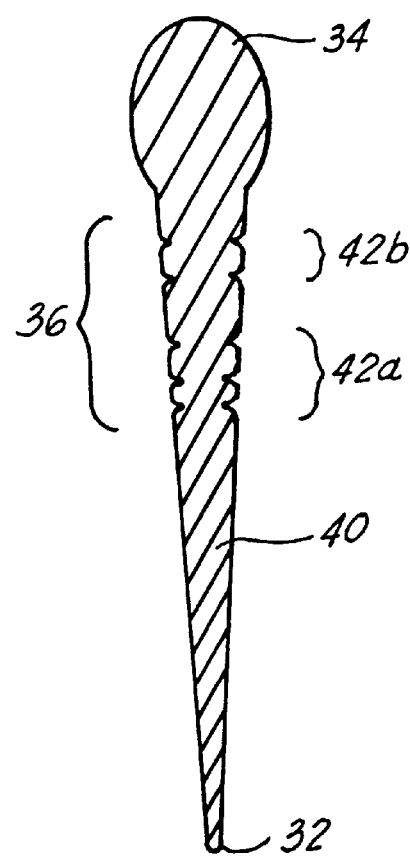
FIG. 3 is a sectional view of the embodiment of the embodiment of the present invention illustrated in FIG. 2, taken along the line 3—3 in that view.
Figure 4:
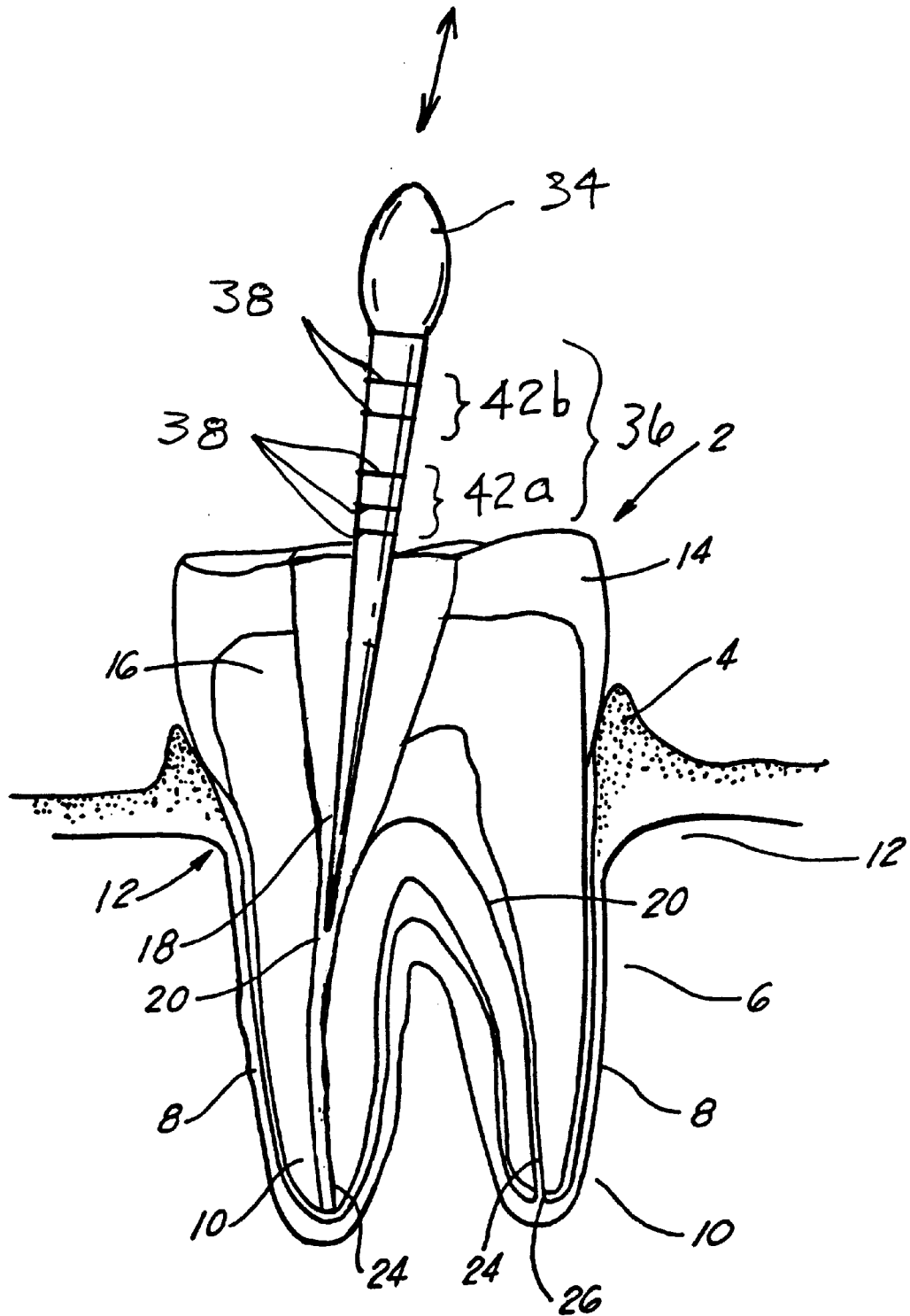
FIG. 4 is a pictorial view, partially in section, of the dental point being inserted into the canal according to the present invention.

Referring now to FIG. 2, a dental point utilized according to the method of the present invention is illustrated. The present invention utilizes in a root canal (endodontic procedure) an absorbent dental point 30 (more commonly referred to as a paper point). Absorbent dental points are conventionally 28 mm to 30 mm in length, as measured from tip 32 to head end 34, and are available from a variety of sources such as Johnson & Johnson, Caulk, Kerr and Dia-Dent. Absorbent dental point 30 used according to the present invention is illustrated as including a graduated depth scale 36 having indicators 38 disposed in ascending or descending relation on shaft 40 of point 30. Indicators may be placed upon point 30 in a variety of ways, well known in the art, including marking by dyes or inks or by such as scribing an imprint or indentation (e.g., engraving) into the surface of the shaft 40.

In a preferred method of use in an endodontic procedure, the present invention makes use of a scale 36 which is made up of depth indicators 38, placed on point 30 in separated groupings, 42a and 42b. In the illustrated embodiment of dental point 30, indicators 38 are spaced at locations indicating a depth (or operational length of point 30 below the specific indicator) of 18, 19, and 20 mm and 22 and 24 mm, as measured from tip 32. As should be appreciated, during the carrying out of a root canal procedure, the mouth cavity becomes quite congested with equipment and instruments, including the suction tube for aspirating debris and fluids from the site, a frame and rubber dam around the subject tooth to shield the rest of the mouth from by-products of the procedure and the dentists fingers and instruments as the procedure is carried out. By providing scale 36 having separate groupings (42a and 42b) of indicators 38, a determination of the depth of the tip 32 of point 30 is more readily observed. As was previously discussed, drying of the cleaned canal 24 requires the same precise use of instrument in order that the tip 32 does not intrude beyond apical foramen 26 causing injury or trauma to periodontium 8. The inclusion of a readily observable and readable scale on the point 30 allows the dental surgeon to precisely confine the drying activity of point 30 within the working distance established as previously discussed. By being able to rely on the readable scale 36, resort to repeated placement of cotton pliers on points 30 is avoided, thereby greatly accelerating the procedure and offering the avoidance of error in the cumbersome use of the plier-loaded point.

In the embodiment wherein three indicators are placed in a grouping (at one millimeter intervals in the illustrated embodiment) as at 42a and two indicators are placed in a grouping (at a two millimeter spacing in the illustrated embodiment) as at 42b, the observation and distinguishing the depth value of a particular indicator 38 on scale 36 as determinative of the depth of tip 32 is readily accomplished. Since the depth indicators 38 of grouping 42a are at one millimeter increments, this grouping is readily differentiated from grouping 42b, in which lines are spaced in two millimeter increments. Likewise, since the numbers of depth indicators 38 within each grouping are limited to two and three indications (i.e., a different number), the distinguishing of the relevant indicator 38 on scale 34 and the accurate measurement of the depth of the canal is readily accomplished.

One skilled in the art will recognize that distinguishable groups of other combinations and values of indicators 38 are within the scope of the present invention. Since the absorbent dental point of the present invention allows the dentist to quickly and reliably measure the depth of the root canal on each and every insertion of a point 30 into the root canal, the effective cleaning, drying and coating of a canal may be reliably performed.

As will be apparent to persons skilled in the art, various additional modifications, adaptations and variations of the foregoing specifically disclosed embodiments and methods of coating removal may be made without departing form the objectives and scope of the present invention. Various modifications and changes may be made to the embodiments disclosed herein by those skilled in the art and such are contemplated by the present invention and are to be understood as included within the spirit and scope of the appended claims.

What is claimed is:

1. In an endodontal procedure, a method of cleaning a root canal with an absorbent dental point comprising;

inserting an absorbent dental point having a shaft portion terminating at its respective ends in a tip portion and a head portion into a root canal;

said shaft portion of said dental point having a cross section of decreasing diameter from said head portion to said tip portion;

said shaft portion of said dental point having a depth scale disposed on said shaft, said scale having an indicator inscribed on said shaft designating a prescribed distance on said shaft with respect to said tip;

inserting said shaft portion of said dental point into the root canal to a predetermined depth corresponding to an indicator on said depth scale.

2. An endodontal procedure in accordance with claim 1 wherein said scale includes a group of a plurality of indicators, wherein each of said indicators are disposed in uniform increments successively with respect to said tip.

3. An endodontal procedure in accordance with claim 2 wherein said scale includes a second group of a plurality of indicators, wherein each of said second group of indicators are disposed in uniform increments successively with respect to said tip.

4. An endodontal procedure in accordance with claim 3 wherein said indicators in said second group are spaced in increments at least twice the spacing of said indicators of said first group.

5. An endodontal procedure in accordance with claim 3 wherein said first group of indicators include three indicators spaced at 18, 19 and 20 millimeters respectively from said tip of said shaft.

6. An endodontal procedure in accordance with claim 3 wherein said second group of indications include two indicators spaced at 22 and 24 millimeters, respectively from said tip of said shaft.

7. An endodontal procedure in accordance with claim 1 wherein said indicator is a line on said shaft, substantially perpendicular to the axis of said shaft.

8. An endodontal procedure in accordance with claim 7 wherein said line is disposed circumferentially around said shaft.

9. An endodontal procedure in accordance with claim 7 wherein said line is printed on said shaft.

10. An endodontal procedure in accordance with claim 7 wherein said line is engraved on said shaft.

* * * * *